United States Patent
Smit et al.

(10) Patent No.: US 9,315,404 B2
(45) Date of Patent: Apr. 19, 2016

(54) PROCESS FOR REDUCING INORGANICS FROM ANIONIC SURFACTANT SOLUTIONS

(75) Inventors: Mark R. Smit, Midland, MI (US); Edward D. Daugs, Midland, MI (US); Raymond M. Collins, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 328 days.

(21) Appl. No.: 13/989,929

(22) PCT Filed: Dec. 5, 2011

(86) PCT No.: PCT/US2011/063316
§ 371 (c)(1),
(2), (4) Date: Jul. 11, 2013

(87) PCT Pub. No.: WO2012/078521
PCT Pub. Date: Jun. 14, 2012

(65) Prior Publication Data
US 2014/0054223 A1    Feb. 27, 2014

Related U.S. Application Data

(60) Provisional application No. 61/420,585, filed on Dec. 7, 2010.

(51) Int. Cl.
| | | |
|---|---|---|
| *C07C 309/00* | (2006.01) | |
| *C02F 9/00* | (2006.01) | |
| *B01D 61/02* | (2006.01) | |
| *C07C 303/44* | (2006.01) | |

(52) U.S. Cl.
CPC .............. *C02F 9/00* (2013.01); *B01D 61/027* (2013.01); *C07C 303/44* (2013.01)

(58) Field of Classification Search
CPC ......... B01D 61/02; C07C 303/44; C11D 1/12
USPC ........................................................ 562/101
See application file for complete search history.

(56) References Cited

U.S. PATENT DOCUMENTS

| | | | | |
|---|---|---|---|---|
| 3,275,682 | A | * 9/1966 | Bakker | ............... C07C 43/12 562/111 |
| 6,183,648 | B1 | * 2/2001 | Kozak et al. | ............... 210/651 |
| 2003/0187295 | A1 | 10/2003 | Schaefer et al. | |

FOREIGN PATENT DOCUMENTS

| | | |
|---|---|---|
| JP | 1992149169 | 5/1992 |
| WO | WO 02/055562 | 7/2002 |

OTHER PUBLICATIONS

Archer et al., Environ. Sci. Technol. 1999, 33, 2758-2764.*
EP Office Action dated Aug. 6, 2013; from EP counterpart Application No. 11794382.9.
PCT Search Report from PCT counterpart Application No. PCT/US11/63316.
IPRP dated Mar. 20, 2013; from PCT counterpart Application No. PCT/US11/63316.
Chinese First Office Action dated Nov. 4, 2014 for counterpart Chinese Application No. 201180058921.8, 3 pages.
Response to Chinese First Office Action dated Nov. 4, 2014 filed Mar. 19, 2015 for counterpart Chinese Application No. 201180058921.8, 4 pages.
Chinese Second Office Action dated Jul. 6, 2015; from Chinese counterpart Application No. 201180058921.8.
Response to Chinese Office Action dated Aug. 27, 2015; from Chinese counterpart Application No. 201180058921.8.
Japanese Office Action dated Oct. 27, 2015; from Japanese counterpart Application No. 2013-543236.

* cited by examiner

*Primary Examiner* — Porifirio Nazario Gonzalez
*Assistant Examiner* — Kofi Adzamli

(57) ABSTRACT

A process comprising contacting deionized water with one or more Strecker sulfonation reaction products of one or more halogenated alkyl ethers in the presence of sulfite, wherein the one or more Strecker sulfonation reaction products each comprise one or more inorganic salts on a dry basis and one or more surfactant components, form a filtration mixture; loading the filtration mixture into a high pressure filtration system containing a membrane having a membrane molecular weight cutoff allowing preferential passage of the inorganic salts, for example, of greater than or equal to 200 Daltons; wherein the high pressure filtration system is operated at a pressure greater than ambient pressure and is configured to cause crossflow of the filtration mixture along a surface of the membrane resulting in a permeate solution which substantially passes through the membrane and a retentate solution which substantially does not pass through the membrane; wherein the permeate comprises less than or equal to 15 weight percent surfactant component, based on the weight of the filtration mixture is provided.

14 Claims, No Drawings

PROCESS FOR REDUCING INORGANICS FROM ANIONIC SURFACTANT SOLUTIONS

FIELD OF THE INVENTION

The invention relates to a process for removing inorganic salts from aqueous anionic surfactant solutions. More particularly, the invention relates to salt removal using membrane filtration.

BACKGROUND OF THE INVENTION

Anionic disulfonate surfactants may be prepared by Strecker sulfonation of alkyl di-chlorides with hydrophobic tail lengths of eight to sixteen carbons. Such surfactants contain excess inorganic salts as reaction by-products. The reaction may be generally described by equation (1) below:

$$RCl_2 + 2M_2SO_3 \rightarrow R(SO_3)_2M + MCl, \quad (1)$$

where M is a metal such as Na and/or K, and R is an alkyl group having between eight and sixteen carbons.

Strecker sulfonation may also be used to sulfonate halogenated alkyl ethers. Halogenated alkyl ethers may be obtained from the acid catalyzed etherification of halogenated alkyl alcohols with α-olefins. For examples, mono- and di-sulfonate surfactants may be produced from Strecker sulfonation of alkyl ethers of 1,3-dichloro-2-propanol (DCP), as shown in equation (2):

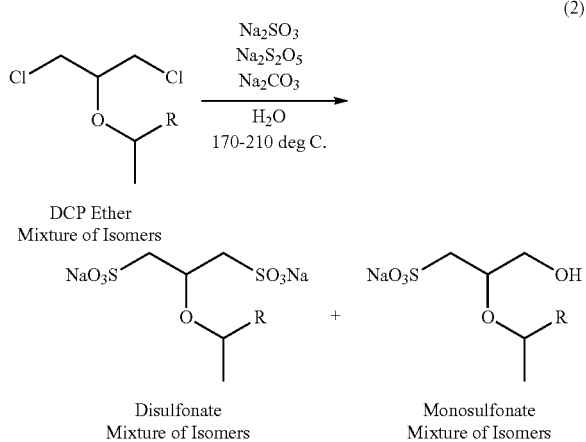

(2)

The reaction shown in equation (2) may be catalyzed by one or more metal halides, including for example sodium iodide. While equation (2) illustrates the DCP ether as being chlorinated, such Strecker sulfonation processes may be carried out with ethers having other halogen substituents, including for example, fluorine, iodine and bromine.

Inorganic salts are a by-product of such Strecker sulfonation processes. In fact, inorganic salts, typically sodium chloride, sodium sulfite and sodium sulfate, may constitute between 50 and 60% by weight of the sulfonation process product on a dry basis. Other reaction products of the Strecker process shown in equation (2) include non-polar organic species, such as the unreacted halogenated alkyl ethers, alkyl alcohols from competitive hydrolysis, and long chain alkenes from dimerization of the α-olefin during etherification.

Such high levels of inorganic salts in surfactant solutions, however, may limit the use of the disulfonate surfactants in some applications, such as emulsion polymerization, cleaning formulations, or personal care product formulations, because inorganic salts may affect surfactant properties. Nevertheless, such disulfonate surfactants display other properties, such as biodegradability, hydrolytic and formulation stability, which are highly desirable.

Inorganic salts have been removed from anionic surfactant solutions by electrodialysis using a hydrophilic neutral membrane and a cation exchange membrane. Such removal process requires specialized processing equipment which significantly raises the cost of producing surfactants for applications where high inorganic salt levels cannot be tolerated. An additional drawback to such technology for inorganic salt removal from anionic surfactant solutions is the generation of a large volume waste stream, typically four to six times the initial volume of the surfactant solution to be treated, containing low levels of surfactant product, along with the associated product loss. Consequently, a commercially facile and efficient method to remove or reduce the amount of residual inorganic salts in disulfonate alkyl surfactant solutions, particularly those arising from the sulfonation of halogenated alkyl ethers would be desirable.

In addition to lowering the salt content of disulfonate surfactants, it is often desirable to produce aqueous concentrates of surfactants, especially because Strecker sulfonation process produces surfactant solutions having a relatively low surfactant concentration, i.e., ranging from 5 wt % to 20 wt % surfactant. Therefore, an economical and commercially practical process for concentrating the surfactant in disulfonate surfactant solutions would also be highly desirable.

SUMMARY OF THE INVENTION

The instant invention is a process for reducing or removing inorganic salts from Strecker sulfonation reaction products.

In one embodiment, the instant invention provides a process comprising: contacting deionized water with one or more Strecker sulfonation reaction products of one or more halogenated alkyl ethers in the presence of sulfite, wherein the one or more Strecker sulfonation reaction products each comprise one or more inorganic salts on a dry basis and one or more surfactant components, form a filtration mixture; loading the filtration mixture into a high pressure stirred system containing a membrane having a nanofiltration membrane molecular weight cutoff that allows preferential transport of the inorganic salts through the membrane while retaining the surfactant product of, for example, greater than 200 Daltons; wherein the high pressure system is operated at a pressure greater than ambient pressure and is configured to cause crossflow of the filtration mixture along a surface of the nanofiltration membrane resulting in a permeate solution which passes through the nanofiltration membrane and a retentate solution which does not pass through the nanofiltration membrane; wherein the permeate comprises less than or equal to 15 weight percent surfactant component, based on the weight of the filtration mixture.

In an alternative embodiment, the instant invention further provides a process comprising: selecting one or more Strecker sulfonation reaction products of one or more halogenated alkyl ethers in the presence of sulfite, wherein the one or more Strecker sulfonation reaction products each comprise one or more inorganic salts on a dry basis and one or more surfactant components; contacting the one or more Strecker sulfonation reaction products with one or more non-polar organic solvents, including but not limited to ethyl acetate, aliphatic and or aromatic hydrocarbons, ethers, ester, and combinations thereof to form an extraction mixture; allowing the extraction mixture to separate into an aqueous phase and an organic phase; and separating the aqueous phase from the organic phase; adding deionized water to the aqueous phase to form a filtration mixture; loading the filtration mixture into a high pressure filtration apparatus containing a nanofiltration membrane having a membrane molecular weight cutoff, for example, of greater than or equal to 200 Daltons; wherein the high pressure system is operated at a pressure greater than ambient pressure and is configured to cause crossflow of the filtration mixture along a surface of the nanofiltration membrane resulting in a permeate solution which passes through the membrane and a retentate solution which does not pass through the nanofiltration membrane; wherein the permeate comprises less than or equal to 15 weight percent surfactant component, based on the weight of the filtration mixture.

In an alternative embodiment, the instant invention provides a process, in accordance with any of the preceding embodiments, except that the one or more halogenated alkyl ethers comprise one or more alkyl ethers of 1,3-dichloro-2-propanol wherein the alkyl group is selected from the group of alkyls having eight or more carbon atoms.

In an alternative embodiment, the instant invention provides a process, in accordance with any of the preceding embodiments, except that the high pressure filtration apparatus is operated at a pressure from 200 psi to 1000 psi.

In an alternative embodiment, the instant invention provides a process, in accordance with any of the preceding embodiments, except that the high pressure filtration apparatus is operated at a temperature from 25 to 55° C.

In an alternative embodiment, the instant invention provides a process, in accordance with any of the preceding embodiments, except that the process further comprises: removing aqueous permeate solution from the high pressure filtration apparatus; bringing the pressure of the high pressure system to ambient pressure; adding to the high pressure system a mass of deionized water substantially equal to the weight of the permeate solution removed from the high pressure system; raising the pressure of the high pressure system to a pressure greater than ambient pressure.

In an alternative embodiment, the instant invention provides a process, in accordance with any of the preceding embodiments, except that the retentate solution consists of less than or equal to 1 weight percent inorganic salts based on the total weight of the retentate solution.

In an alternative embodiment, the instant invention provides a process, in accordance with any of the preceding embodiments, except that the permeate solution comprises less than or equal to 2 weight percent total surfactant component based on the total weight of the permeate solution.

In an alternative embodiment, the instant invention provides a process, in accordance with any of the preceding embodiments, except that the process further comprises: contacting the one or more Strecker sulfonation reaction products with an oxidizing agent prior to formation of the filtration mixture.

In an alternative embodiment, the instant invention provides a process, in accordance with any of the preceding embodiments, except that the process further comprises: filtering the filtration mixture with a non-nanofiltration filter having a particle retention size of equal to or greater than 1 micron prior to loading the filtration mixture into the high pressure system apparatus.

In an alternative embodiment, the instant invention provides a process, in accordance with any of the preceding embodiments, except that the one or more inorganic salts are selected from sodium sulfite, sodium bisulfite, sodium sulfate, sodium bisulfate, and sodium chloride, and their potassium counterparts.

In an alternative embodiment, the instant invention provides a process, in accordance with any of the preceding embodiments, except that the one or more Strecker sulfonation reaction products each comprise between 40 and 60 percent by weight on a dry basis of the one or more inorganic salts.

In an alternative embodiment, the instant invention provides a process, in accordance with any of the preceding embodiments, except that the extraction mixture comprises between 25 and 60 percent by weight on a dry basis of the one or more Strecker sulfonation reaction products.

In an alternative embodiment, the instant invention provides a process, in accordance with any of the preceding embodiments, except that the surfactant component of the one or more Strecker sulfonation products each comprises one or more disulfonated alkyl ethers, one or more monosulfonated alkyl ethers, or a combination thereof.

In an alternative embodiment, the instant invention provides a process, in accordance with any of the preceding embodiments, except that the retentate solution comprises between 10 and 50 percent by weight of a surfactant component.

In an alternative embodiment, the instant invention provides a process, in accordance with any of the preceding embodiments, except that the surfactant component comprises one or more disulfonated alkyl ethers, one or more monosulfonated alkyl ethers, or combinations thereof.

In an alternative embodiment, the instant invention provides a process, in accordance with any of the preceding embodiments, except that the one or more halogenated alkyl ethers comprise one or more dihalogenated alkyl ethers.

DETAILED DESCRIPTION OF THE INVENTION

The instant invention is a process for reducing or removing inorganic salts from a Strecker sulfonation reaction product solution.

In one embodiment, the instant invention provides a process comprising: contacting deionized water with one or more Strecker sulfonation reaction products of one or more halogenated alkyl ethers in the presence of sulfite, wherein the one or more Strecker sulfonation reaction products each comprise one or more inorganic salts on a dry basis and one or more surfactant components, form a filtration mixture; loading the filtration mixture into a high pressure filtration apparatus containing a nanofiltration membrane having a membrane molecular weight cutoff, for example, of greater than or equal to 200 Daltons; wherein the high pressure system is operated at a pressure greater than ambient pressure and is configured to cause crossflow of the filtration mixture along a surface of the nanofiltration membrane resulting in a permeate solution which substantially passes through the membrane and a retentate solution which substantially does not pass through the nanofiltration membrane; wherein the permeate comprises less than or equal to 15 weight percent surfactant component, based on the weight of the filtration mixture.

In an alternative embodiment, the instant invention provides a process comprising: selecting one or more Strecker sulfonation reaction products of one or more halogenated alkyl ethers in the presence of sulfite, wherein the one or more Strecker sulfonation reaction products each comprise one or more inorganic salts on a dry basis and one or more surfactant components; contacting the one or more Strecker sulfonation reaction products with one or more non-polar organic solvents, including but not limited to ethyl acetate, aliphatic and or aromatic hydrocarbons, ethers, esters and combinations thereof to form an extraction mixture; allowing the extraction mixture to separate into an aqueous phase and an organic phase; and separating the aqueous phase from the organic phase to provide a filtration mixture; loading the filtration mixture into a high pressure filtration system containing a nanofiltration membrane having a membrane molecular weight cutoff of greater than or equal to, for example, 200 Daltons; wherein the high pressure system is operated at a pressure greater than ambient pressure and is configured to cause crossflow of the filtration mixture along a surface of the nanofiltration membrane resulting in a permeate solution which substantially passes through the nanofiltration membrane and a retentate solution which substantially does not pass through the nanofiltration membrane; wherein the permeate comprises less than or equal to 15 weight percent surfactant component, based on the weight of the filtration mixture.

The one or more Strecker sulfonation reaction products of one or more halogenated alkyl ethers in the presence of sodium sulfite may comprise one or more surfactant components selected from disulfonated alkyl ethers, monosulfonated alkyl ethers, and combinations thereof.

In some embodiments of the invention, the one or more halogenated alkyl ethers comprise one or more dihalogenated alkyl ethers.

The disulfonated alkyl ethers may include any surfactant having the general formula $(NaO_3S)_2R'OR$, where R' is an alkyl group having 3 or more carbon atoms and R is a linear or branched or mixture thereof alkyl group having 8 or more carbon atoms. R' may be, in some embodiments, a propyl, butyl, pentyl or hexyl group. R may be, in some embodiments, an alkyl group having between 8 and 16 carbon atoms.

The monosulfonated alkyl ethers may include any surfactant having the general formula $(NaO_3S)(OH)R'OR$, where R' is an alkyl group having 3 or more carbon atoms and R is a linear or branched or mixture thereof alkyl group having 8 or more carbon atoms. R' may be, in some embodiments, a propyl, butyl, pentyl or hexyl group. R may be, in some embodiments, an alkyl group having between 8 and 16 carbon atoms.

The starting feedstock for the Strecker sulfonation reaction may be selected from any mono- or dihalogenated alkyl ethers having the general formula $XnR'OCR$, where n may be 1 or 2, X is a halogen, is an alkyl group having 3 or more carbon atoms and R is a linear or branched or mixture thereof alkyl group having 8 or more carbon atoms. In preferred embodiments, starting feedstock is a mixture of isomers of the alkyl ethers of 1,3-dichloro-2-propanol. In certain specific embodiments, the one or more dihalogenated alkyl ethers comprise one or more alkyl ethers of 1,3-dichloro-2-propanol wherein the alkyl group has eight or more carbon atoms.

Nanofiltration membranes are useful in the inventive process have a membrane molecular weight cutoff that allow preferential passage of inorganic salts including but not limited to sodium chloride, sodium sulfite, sodium sulfate, and their potassium counterparts, for example, of greater than or equal to 200 Daltons. All individual values and subranges greater than or equal to 200 Daltons are included herein and disclosed herein; for example, the membrane molecular weight may be from a lower limit of 200, 300, 400, 450, or 500 Daltons.

The inventive process produces a permeate solution which comprises less than or equal to 15 weight percent surfactant component, based on the weight of the filtration mixture. All individual values and subranges less than or equal to 15 weight percent are included herein and disclosed herein; for example, the amount of surfactant component in the permeate solution may be from an upper limit of 1, 3, 5, 10, or 15 weight percent.

As used herein, the term "permeate solution which substantially passes through the nanofiltration membrane" means that part of the filtration mixture which comprises passes through the nanofiltration membrane and carries with it across the membrane no more than 15 weight percent surfactant component present in the filtration mixture. As used herein, the term "retentate solution which substantially does not pass through the nanofiltration membrane" means that part of the filtration mixture that remains on the upstream side of the nanofiltration membrane and that comprises at least 85 weight percent of the surfactant component present in the filtration mixture.

The high pressure filtration system useful in the inventive process, includes, for example, a high pressure stirred cell that may be operated at a pressure from 200 psi to 1000 psi. All individual values and subranges from 200 psi to 1000 psi are included herein and disclosed herein; for example, the pressure may be from a lower limit of 200, 300, 400, 500, 600, 700, 800, or 900 psi and from an upper limit of 300, 400, 500, 600, 700, 800, 900, or 1000 psi. For example, the pressure may range from 200 to 1000 psi, or in the alternative, the pressure may range from 400 to 800 psi, or in the alternative, the pressure may range from 600 to 1000 psi, or in the alternative, the pressure may range from 300 to 700 psi.

The high pressure filtration system, such as a high pressure stirred cell useful in the inventive process may be operated at a temperature from 25 to 55° C. All individual values and subranges from 25 to 55° C. are included herein and disclosed herein; for example, the temperature may be from a lower limit of 25, 35, or 45° C. and from an upper limit of 35, 45, or 55° C. For example, the temperature may range from 25 to 55° C., or in the alternative, the temperature may range from 25 to 45° C., or in the alternative, the temperature may range from 35 to 55° C., or in the alternative, the temperature may range from 35 to 45° C.

In some embodiments, the inventive process further comprises bringing the pressure of the high pressure filtration system to ambient pressure; removing the permeate solution from the high pressure system; adding to the high pressure system a mass of deionized water substantially equal to the weight of the permeate solution removed; raising the pressure of the high pressure system to a pressure greater than ambient pressure.

The retentate solution formed in embodiments of the inventive process comprises less than or equal to 1 weight percent inorganic salt content based on the total weight of the retentate solution. All individual values and subranges from less than or equal to 1 weight percent are included herein and disclosed herein; for example, the amount of inorganic salt content in the retentate can be from an upper limit of 0.1, 0.2, 0.3, 0.4, 0.5, 0.6, 0.7, 0.8, 0.9 or 1 weight percent, based on the total weight of the retentate.

The permeate solution formed in embodiments of the inventive process comprises less than or equal to 2 weight percent total surfactant component based on the total weight of the permeate solution. All individual values and subranges from less than or equal to 2 weight percent are included herein and disclosed herein; for example, the amount of surfactant in the permeate solution can be from an upper limit of 0.2, 0.5, 0.8, 1, 1.3, 1.6, 1.9, or 2 weight percent.

One embodiment of the inventive process further comprises: contacting the one or more Strecker sulfonation reaction products with an oxidizing agent prior to formation of the filtration mixture.

In some embodiments, the one or more Strecker sulfonation reaction products each comprise at least 30 percent by weight of one or more inorganic salts on a dry basis. The one or more inorganic salts may be selected from the group of sodium sulfite, sodium bisulfite, sodium bisulfate, sodium sulfate, sodium chloride, and the potassium counter parts, and combinations thereof. In one aspect, the sulfite and bisulfite species may be oxidized to sulfate and bisulfate by addition of, for example, hydrogen peroxide. All individual values and subranges from at least 30 percent by weight are included herein and disclosed herein; for example, the weight percent of the one or more inorganic salts based on the total weight of the one or more Strecker sulfonation reaction products may be from a lower limit of 30, 35, 40, 45, or 50 weight percent to an upper limit of 35, 40, 45, 50, 55, or 60 weight percent on a dry basis. For example, the percent by weight of the one or more inorganic salts may be in the range from 30 to 60 weight percent, or in the alternative, the percent by weight of the one or more inorganic salts may be in the range from 40 to 50 weight percent, or in the alternative, the percent by weight of the one or more inorganic salts may be in the range from 40 to 60 weight percent, or in the alternative the percent by weight of the one or more inorganic salts may be in the range from 50 to 60 weight percent.

One embodiment of the inventive process further comprises: filtering the filtration mixture with a non-nanofiltration filter having a particle retention size of equal to or greater than 1 micron prior to loading the filtration mixture into the high pressure filtration system. All individual values and subranges from equal to or greater than 1 micron are included herein and disclosed herein; for example, the particle retention size can be from an lower limit of 1, 1.2, 1.4, 1.6, 1.8, 2, 2.5 or 3 microns.

The extraction mixture produced in some embodiments of the inventive process comprises from 25 to 60 weight percent inorganic salt on a dry basis of the one or more Strecker sulfonation reaction products. All individual values and subranges from 25 to 60 weight percent inorganic salt are included herein and disclosed herein; for example, the amount of inorganic salt can be from a lower limit of 25, 30, 35, 40, 45, 50, or 55 weight percent to an upper limit of 30, 35, 40, 45, 50, 55, or 60 weight percent. For example, the amount of inorganic salt may be in the range of from 25 to 60 weight percent, or in the alternative, the amount of inorganic salt may be in the range of from 30 to 50 weight percent, or in the alternative, the amount of inorganic salt may be in the range of from 35 to 60 weight percent.

In an alternative embodiment, the instant invention provides a process, in accordance with any of the preceding embodiments, except that the surfactant component of the organic phase and the surfactant component of the one or more Strecker sulfonation products each comprise one or more disulfonated alkyl ethers, one or more monosulfonated alkyl ethers, or a combination thereof.

In an alternative embodiment, the instant invention provides a process, in accordance with any of the preceding embodiments, except that the retentate solution comprises from 10 to 50 percent by weight of a surfactant component. All individual values and subranges from 10 to 50 weight percent inorganic salt are included herein and disclosed herein; for example, the amount of surfactant component can be from a lower limit of 10, 20, 30, 40, or 45 weight percent to an upper limit of 20, 30, 40, 45, or 50 weight percent. For example, the amount of surfactant component may be in the range of from 10 to 50 weight percent, or in the alternative, the amount of surfactant component may be in the range of from 20 to 40 weight percent, or in the alternative, the amount of surfactant component may be in the range of from 35 to 50 weight percent.

In one embodiment of the inventive process, the surfactant component comprises one or more disulfonated alkyl ethers, one or more monosulfonated alkyl ethers, or combinations thereof.

In one embodiment of the inventive process, the one or more halogenated alkyl ethers comprise one or more dihalogenated alkyl ethers.

The one or more non-polar organic solvents may be one or more of any non-polar organic solvent that has poor solubility of the one or more Strecker sulfonation reaction products and good solubility of the Strecker sulfonation organic by-products.

The one or more non-polar organic solvents, in some embodiments, are selected from the group of ethyl acetate, aliphatic and or aromatic hydrocarbons, ethers, and esters. In preferred embodiments, the non-polar organic solvent is ethyl acetate.

The contacting of the one or more Strecker sulfonation reaction products with the one or more organic solvents may be accomplished using any equipment or procedure allowing for mixing of liquids. For example, the contacting may be accomplished in a tank equipped with a mechanical or electromagnetic stirrer, paddle or similar mechanism. Alternatively, the one or more Strecker sulfonation reaction products may be contacted with the one or more organic solvents by turbulent flow through piping or during loading into a vessel. The contacting of the one or more Strecker sulfonation reaction products with the one or more organic solvents may be accomplished batch wise or in a continuous fashion, wherein a stream of the Strecker sulfonation reaction products is mixed with the one or more organic solvents in a mixing zone and transferred to a second settling zone in which phase separation occurs.

The contacting of the one or more Strecker sulfonation reaction products with the one or more organic solvents may occur at any temperature equal to or greater than 0° C. All individual values and subranges from greater than 0° C. are included herein and disclosed herein; for example, the temperature during contacting may be from a lower limit of 0, 10, 20, 25 or 30° C. to an upper limit of 25, 30, 35, 40, 50, or 60° C. For example, the temperature during contacting may be from 10 to 60° C., or in the alternative, from 20 to 50° C., or in the alternative, from 30 to 50° C., or in the alternative from 35 to 55° C.

The contacting of the one or more Strecker sulfonation reaction products with the one or more organic solvents may occur for a period greater than one minute. All individual values and subranges from greater than one minute are included herein and disclosed herein; for example, the contacting time may be from a lower limit of 1, 5, 7, 10, 15, 20, 25 or 30 minutes to an upper limit of 5, 10, 15, 20, 30, 40 or 60 minutes. For example, the contacting time may be from 1 to 60 minutes, or in the alternative, from 5 to 15 minutes, or in the alternative, from 10 to 30 minutes, or in the alternative from 20 to 40 minutes.

The allowing of the extraction mixture to form into an aqueous phase and an organic phase may occur using any appropriate equipment and procedure, including for example, by allowing the extraction mixture to sit unagitated in a tank or similar vessel. Alternatively, the formation of the two phases may be aided through the use of any appropriate equipment or procedure known to those skilled in the art, including for example, subjecting the extraction mixture to centrifugal forces in a cyclone.

The aqueous and organic phases may be separated using any appropriate equipment and procedure, including for example, decanting the organic phase from the aqueous phase. Alternatively, the phase may be separated by siphoning the aqueous phase from a vessel containing the two phases. The phase separation operation may be conducted batchwise or in a continuous fashion, wherein a mixture of the two phases is introduced to a settling zone and each separated phase collected from the upper and lower sections of the settling zone.

In some embodiments, the inventive process further comprises adding sufficient peroxide, generally to a slight excess, to the one or more Strecker sulfonation reaction products, to achieve a positive peroxide test to oxidize sulfite species to sulfate species and form a peroxide-treated/sulfonate mixture; contacting the peroxide-treated/sulfonate mixture with ethyl acetate to form a peroxide-treated/sulfonate/ethyl acetate mixture; allowing the peroxide-treated/sulfonate/ethyl acetate mixture to separate into a water soluble surfactant phase comprising the one or more Strecker sulfonation reaction products wherein undesired non-polar by-products have been removed there from, prior to contacting the Strecker sulfonation reaction product mixture with the filtration system. The separating of the peroxide-treated/sulfonate/ethyl acetate mixture may occur using any of the equipment and procedures discussed previously.

EXAMPLES

The following examples illustrate the present invention but are not intended to limit the scope of the invention. The examples of the instant invention demonstrate that substantial reduction of the inorganic salt content of a sulfonation reaction solution while maintaining efficient recovery of the surfactant may be achieved in accordance with the present invention.

As used in the examples below, the term CX sulfonate reaction product means the reaction product of Equation (2), where X represents the number of carbons in R, an alkyl group. As discussed above, the CR sulfonate reaction product includes both disulfonate and monosulfonate products as well as a variety of by-products. The percent by weight of each of the disulfonate and monosulfonate components are given for each CX sulfonate reaction product, as analyzed by high pressure liquid chromatography.

The feed stream containing mixtures of mono and di-anionic surfactant products are first purified using an ethyl acetate extraction to remove lower molecular weight organic byproducts.

Preparation of Sample 1 by Ethyl Acetate Extraction of C12 Disulfonate Reaction Product:

The product from the reaction of 200.5 grams of 1,3-dichloropropan-2-yloxydodecane, 148.0 grams of sodium sulfate, 52.0 grams of sodium meta-bisulfite, 48.3 grams of sodium carbonate, and 914.3 grams of water at 200° C. for 20 hours was loaded into a 5 L (liter) glass bottom-drain jacketed reactor. 60 ml (milliliter) of 30% aqueous hydrogen peroxide was added to the reactor until a positive peroxide test (using peroxide test strips) was obtained. The reactor mixture was then diluted with 664 grams of ethyl acetate, stirred for 5 minutes at ambient temperature, and then the agitator was stopped and the phases allowed to settle for 37 minutes. The aqueous phase (1493.2 grams) was separated from the organic phase (552.4 grams). The aqueous phase, Sample 1, was used as feed for subsequent membrane nanofiltration.

Description of the Nanofiltration Equipment

A high-pressure stirred cell available from Evonik Industries AG ("Evonik") (Essen, Germany), was used to hold the membrane and establish crossflow of the surfactant solution along the membrane surface. The membranes used are also available from Evonik under the tradename DuraMem™ and are made from P84 asymmetric and crosslinked polyimide, having a rated molecular weight cut-off (MWCO) of 500 Daltons (D). The stirred cell accepts a 90-mm diameter circular membrane cut from a flat sheet, providing 54 $cm^2$ of active membrane area for nanofiltration. Tangential flow of solution along the membrane surface is established by rotating a magnetically coupled, Teflon™-encapsulated stirring disk mounted above the center of the upstream surface of membrane. The membrane is supported on its downstream side by a porous sintered metal disk, which sits above channels designed to drain permeate. Controlled pressure is applied to the upstream solution, or retentate, by regulated compressed gas. For the samples discussed herein, an air cylinder was used. A small electrical resistance panel was installed on the outside of the high pressure stirred cell to heat the cell and its contents. A J-type thermocouple was inserted through the top cover of the cell and immersed in the solution within the cell. The temperature sensed by this thermocouple was used with an electronic controller to regulate heat input.

The stirred cell has a maximum working volume of 270 ml and a maximum working pressure of 69 bar gauge (1000 psi). Stirrer speed may be set in the range from 350 to 500 rpm. A digital magnetic stirrer was used that sensed the actual rotational speed of the stirrer and displayed the speed in comparison to the set point, which was typically 425 rpm. The transmembrane pressure was controlled at 20 bar gauge (about 300 psig) by a series of mechanical pressure regulators. The solution temperature was controlled at 40° C. to maximize the solubility of $Na_2SO_4$ and NaCl in water. Permeate was collected in a glass flask sitting on a top loading electronic balance having accuracy to 0.01 gram. Weights measured by the balance were acquired and recorded at precise time intervals. These weights were later converted to the cumulative volume of permeate at specific times using the specific gravity measured by a hydrometer. Cumulative volumes were numerically differentiated to obtain the volumetric flow rate and flux of permeate.

The volumes beginning in the nanofiltration process determined the ratio of solvent added at each cycle and the number of cycles required to obtain the desired low concentration of inorganic salts in retentate. The stirred cell was depressurized and opened to add charges of fresh distilled water. A small (1 to 3 g) sample of retentate was withdrawn between cycles and analyzed to determine the retentate's concentration of sulfonates and salts. The weights of initial feed solution, individual permeates, charges of distilled water, and final retentate were measured. The weight of permeate was used on each cycle to determine the weight of distilled water to be added to restore the original working volume of solution. When retentate contained sufficiently low concentrations of inorganic salts, it was concentrated by membrane nanofiltration to the starting volume of surfactant solution, or less until the permeate flux appeared impractically low.

Nanofiltration of C12 Surfactant Solution:

Sample 1 was filtered using a WHATMAN Gf/B glass microfiber filter (having a particle retention size of 1.0 micron, available from GE Healthcare, a division of General Electric Company) resulting in Sample 2. 146.39 grams of Sample 2 and 127.30 grams of deionized water were loaded into a high pressure stirred cell containing a DuraMem™ 500 membrane. The stirred cell was pressurized to 20 bar gauge (about 300 psig), stirred at 425 rpm and warmed to a temperature from 34 to 40° C. 127.05 grams of permeate, Permeate sample 1, were removed over 74 minutes, followed by recovery of 1.21 grams of retentate, Retentate sample 1. The stirred cell was then charged with 122.24 grams of deionized water and the pressure reapplied. 126.79 g of permeate, Permeate sample 2, was removed (following a total time 130 minutes) and 1.1 grams of retentate, Retentate sample 2, was removed from the stirred cell. The stirred cell was then charged with 125.02 grams of deionized water and the pressure again reapplied. After a total operation time of 178 minutes, 127.20 grams of permeate, Permeate sample 3, was removed and 0.98 grams of retentate, Retentate sample 3, was recovered from the cell. The stirred cell was charged with 123.55 grams of deionized water and the pressure again reapplied. Following a total operational time of 222 minutes, 126.6 grams of permeate, Permeate sample 4, was removed and 0.99 grams of retentate, Retentate sample 4, was recovered. The stirred cell was then charged with 125.85 grams of deionized water and the pressure reapplied. After 129.30 grams of permeate, Permeate sample 5, was removed (following a total operational time of 264 minutes), 1.11 grams of the retentate, Retentate sample 5, was recovered and the pressure reapplied to the stirred cell. An additional 47.48 grams of permeate, Permeate sample 6, was removed at a total operational time of 300 minutes leaving 78.04 grams of retentate, Retentate sample 6. Table 1 provides the compositional analysis for each of Sample 1, Retentate samples 1-6 and Permeate samples 1-6.

performed using an Alltech 2000 Evaporative Light Scattering Detector with a drift tube temperature of 75° C. and a 2.2 mL/min nitrogen flow, an ESA Corona plus corona discharge detector operating at 35 psi nitrogen, 30° C., 200 picoAmps with a low response filter. The detector response curve, which was quadratic, was calibrated using standard solutions of each of the isolated sulfonates. Sulfonate reaction product samples were diluted, typically from 1:10 to 1:100, to ensure the sample concentration was within the calibrated range. Peaks for the positional isomers were summed to give a total component concentration.

Ion Chromatography Analysis

Ion chromatography analysis for determining chloride and sulfate concentrations was carried out on a DIONEX DX-120 ion chromatograph (available from DIONEX CORPORATION) by injecting a 25 µL sample onto a 4×250 mm IonPac AS22 column and eluting at 1.2 mL/min with 4.0 mM sodium carbonate/1.0 mM sodium bicarbonate in 18 mΩ water. The system was calibrated in the range of 0.05 to 5 ppm chloride and 0.1 to 10 ppm sulfate (diluted from 1000 ppm standard solutions of each supplied by Inorganic Ventures, Inc. (Christiansburg, Va.)). Samples for analysis were diluted in 18 mΩ water to within the calibrated range (typically 1:10,000 to 1:100,000 dilutions). Under these conditions, chloride eluted at 4.5 minutes and sulfate eluted at 11.8 minutes The present invention may be embodied in other forms without departing from the spirit and the essential attributes thereof, and, accordingly, reference should be made to the

TABLE 1

| Sample | NaCl, wt % | NaSO4, wt % | C12 Disulfonate, wt % | C12 Monosulfonate, wt % | Inorganic Salts (dry basis), wt % |
|---|---|---|---|---|---|
| Sample 1 | | | 7.6 | 4.6 | |
| Sample 2 | 4.7 | 5.95 | 8.23 | 4.49 | 45.6 |
| Retentate Sample 1 | 2.06 | 3.22 | 7.32 | 4.16 | 31.5 |
| Retentate Sample 2 | 0.71 | 1.36 | 7.16 | 3.73 | 16.0 |
| Retentate Sample 3 | 0.33 | 0.86 | 6.87 | 3.72 | 10.1 |
| Retentate Sample 4 | 0.13 | 0.50 | 6.85 | 3.94 | 5.5 |
| Retentate Sample 5 | 0.05 | 0.27 | 6.96 | 4.31 | 2.7 |
| Retentate Sample 6 | 0.03 | 0.21 | 10.0 | 6.11 | 1.4 |
| Permeate Sample 1 | 2.42 | 2.72 | 0.60 | 0.20 | 86.5 |
| Permeate Sample 2 | 1.22 | 1.6 | 0.21 | 0.07 | 91.0 |
| Permeate Sample 3 | 0.54 | 0.83 | 0.18 | 0.04 | 86.2 |
| Permeate Sample 4 | 0.25 | 0.53 | 0.22 | 0.03 | 75.7 |
| Permeate Sample 5 | 0.09 | 0.22 | 0.21 | 0.04 | 56.8 |
| Permeate Sample 6 | 0.10 | 0.36 | 0.43 | 0.07 | 47.4 |

Test Methods

DCP Sulfonate solutions were prepared according to the process disclosed in U.S. patent application Ser. No. 12/827,165, filed Jun. 30, 2010 and having a priority date of Jul. 16, 2009, the disclosure of which is incorporated herein by reference.

High Pressure Liquid Chromatography

High pressure liquid chromatography (HPLC) analysis for determining DCP-based surfactant concentrations was carried out on a ChemStation controlled Agilent 1100 HPLC system by injecting 20 µL of sample onto a 150 mm×4.6 mm ALTIMA C18 5 micron column at 40° C. and eluting at 1 mL/min with the solvent gradient of 90% A (90/10 water/acetonitrile, 0.01 M ammonium acetate) and 10% B (10/90 water/acetonitrile, 0.01 M ammonium acetate) to 100% B at 22 minutes, as shown in Table 2. Run time was 30 minutes. The C12 Disulfonate eluted at about 7 minutes and the C12 Monosulfonate eluted at about 12 minutes. Detection was appended claims, rather than to the foregoing specification, as indicating the scope of the invention.

We claim:

1. A process comprising:
  conducting a Strecker sulfonation reaction of one or more alkyl ethers of 1,3-dihalo-2-propanol to form a Strecker sulfonation reaction product mixture which comprises disulfonate and monosulfonate surfactant components and one or more inorganic salts;
  contacting deionized water with the Strecker sulfonation reaction product mixture of one or more halogenated alkyl ethers, wherein the alkyl groups of the alkyl ethers comprise from 8 to 16 carbons, in the presence of sulfite, wherein the Strecker sulfonation reaction product mixture to form a filtration mixture;
  loading the filtration mixture into a high pressure filtration system containing a nanofiltration membrane having a membrane molecular weight cutoff allowing preferential passage of inorganic salts of greater than or equal to 200 Daltons;

wherein the high pressure filtration system is operated at a pressure greater than ambient pressure and is configured to cause crossflow of the filtration mixture along a surface of the nanofiltration membrane resulting in a permeate solution which substantially passes through the nanofiltration membrane and a retentate solution which substantially does not pass through the nanofiltration membrane;

wherein the permeate comprises less than or equal to 15 weight percent surfactant components, based on the total weight of the surfactant components in the filtration mixture.

2. A process comprising:
conducting a Strecker sulfonation reaction of one or more alkyl ethers of 1,3-dihalo-2-propanol to form a Strecker sulfonation reaction product mixture which comprises disulfonate and monosulfonate surfactant components and one or more inorganic salts, wherein the alkyl groups of the alkyl ethers comprise from 8 to 16 carbon atoms, in the presence of sulfite, contacting the Strecker sulfonation reaction product mixture with one or more organic solvents selected from the group consisting of ethyl acetate, aliphatic and aromatic hydrocarbons, ethers, esters, and combinations thereof to form an extraction mixture;

allowing the extraction mixture to separate into an aqueous phase and an organic phase; and separating the aqueous phase from the organic phase;

adding deionized water to the aqueous phase to form a filtration mixture:

loading the filtration mixture into a high pressure filtration system containing a nanofiltration membrane having a membrane molecular weight cutoff of greater than or equal to, for example, 200 Daltons;

wherein the high pressure system is operated at a pressure greater than ambient pressure and is configured to cause crossflow of the filtration mixture along a surface of the nanofiltration membrane resulting in a permeate solution which substantially passes through the nanofiltration membrane and a retentate solution which substantially does not pass through the nanofiltration membrane;

wherein the permeate comprises less than or equal to 15 weight percent surfactant components, based on the total weight of the surfactant components in the filtration mixture.

3. The process according to claim 1, wherein the one or more halogenated alkyl ethers comprise one or more alkyl ethers of 1,3-dichloro-2-propanol wherein the alkyl group is selected from the group of alkyls having eight or more carbon atoms.

4. The process according to claim 1, wherein the high pressure filtration system is a operated at a pressure from 200 psi to 1000 psi.

5. The process according to claim 1, wherein the high pressure filtration system is operated at a temperature from 25 to 55° C.

6. The process according to claim 1, further comprising:
bringing the pressure of the high pressure filtration system to ambient pressure;
removing the permeate solution from the high pressure filtration system;
adding to the high pressure filtration system a mass of deionized water substantially equal to the weight of the permeate solution removed from the high pressure system;
raising the pressure of the high pressure system to a pressure greater than ambient pressure.

7. The process according to claim 1, wherein the retentate solution comprises less than or equal to 1 weight percent inorganic salt content based on the total weight of the retentate solution.

8. The process according to claim 1, further comprising:
contacting the Strecker sulfonation reaction product mixture with an oxidizing agent prior to formation of the filtration mixture.

9. The process according to claim 1, further comprising:
filtering the filtration mixture with a non-nanofiltration filter having a particle retention size of equal to or greater than 1 micron prior to loading the filtration mixture into the high pressure filtration system.

10. The process according to claim 1, wherein the one or more inorganic salts are selected from sodium sulfite, sodium bisulfate, sodium sulfate, sodium bisulfate, and sodium chloride, and their potassium counterparts.

11. The process according to claim 1, wherein the Strecker sulfonation reaction product mixture each comprise between 40 and 60 percent by weight on a dry basis of the one or more inorganic salts.

12. The process according to claim 1, wherein the extraction mixture comprises between 25 and 60 percent by weight on a dry basis of the Strecker sulfonation reaction product mixture.

13. The process of according to claim 1, wherein the surfactant component of the Strecker sulfonation reaction product mixture each comprise one or more disulfonated alkyl ethers, one or more monosulfonated alkyl ethers, or a combination thereof.

14. The process according to claim 1, wherein the retentate solution comprises between 10 and 50 percent by weight of a surfactant component.

* * * * *